United States Patent [19]

Palepu et al.

[11] Patent Number: 5,130,305
[45] Date of Patent: Jul. 14, 1992

[54] CYCLOPHOSPHAMIDE - SODIUM BICARBONATE LYOPHILIZATES

[75] Inventors: Nageswara R. Palepu, Dublin; Julie A. Hutt, Columbus, both of Ohio

[73] Assignee: Erbamont, Inc., Dublin, Ohio

[21] Appl. No.: 597,965

[22] Filed: Oct. 15, 1990

Related U.S. Application Data

[63] Continuation-in-part of Ser. No. 270,707, Nov. 14, 1988, abandoned.

[51] Int. Cl.$^5$ ................. A61K 31/66; A61K 33/00
[52] U.S. Cl. ............................. 514/110; 424/717
[58] Field of Search ................. 514/110; 424/717

[56] References Cited

U.S. PATENT DOCUMENTS

| | | | |
|---|---|---|---|
| 4,537,883 | 8/1985 | Alexander et al. | 514/110 |
| 4,659,699 | 4/1987 | Francis | 514/53 |
| 5,036,060 | 7/1991 | Alam et al. | 514/110 |

FOREIGN PATENT DOCUMENTS 0401894 12/1990 European Pat. Off. .

OTHER PUBLICATIONS

Kovalcik et al., "The Stability of Cyclophosphamide in Lyophilized Cakes", Journal of Parenteral Science and Technology, vol. 42, No. 1, 1188, pp. 29-37 (1988).

*Primary Examiner*—Frederick E. Waddell
*Assistant Examiner*—Raymond J. Henley, III
*Attorney, Agent, or Firm*—Thompson, Hine and Flory

[57] ABSTRACT

A stable rapidly dissoloving lyophilized and hydrated composition of cyclophosphamide and sodium bicarbonate is provided which contains an amount of water which is at least equimolar to the combined amount of cyclophosphamide and sodium bicarbonate in the composition and the weight ratio of cyclophosphamide to sodium bicarbonate is about 1:0.5 to 1:1.5; the composition is preferably prepared from a solution containing at least 1% (W/V) weight sodium bicarbonate.

13 Claims, No Drawings

CYCLOPHOSPHAMIDE - SODIUM BICARBONATE LYOPHILIZATES

CROSS-REFERENCE TO RELATED APPLICATION

This application is a continuation-in-part of U.S. application Ser. No. 270,707, filed Nov. 14, 1988, now abandoned.

BACKGROUND OF THE INVENTION

The present invention relates to a novel lyophilized composition containing cyclophosphamide and sodium bicarbonate as an excipient.

U.S. Pat. No. 4,537,883 to Alexander et al. (Mead Johnson & Co.) discloses various lyophilizates of cyclophosphamide. These lyophilizates are prepared by lyophilizing a solution of cyclophosphamide and one or more excipients and re-hydrating the product such that it contains about 4% moisture. The patent is based upon a comparative study of lyophilizate cakes and the dissolution time for lyophilizates of cyclophosphamide prepared using a number of excipients. The study concludes that the lyophilizate prepared with mannitol gives a better cake and faster dissolution time than the lyophilizates prepared with other excipients. The patent also teaches that the lyophilized cyclophosphamide-mannitol composition exhibits better thermal stability if it contains an equimolar amount of water based on cyclophosphamide. The preferred lyophilizate contains 20 parts cyclophosphamide, 1.25 to 2 parts water and 10 to 85 parts mannitol. Among the excipients evaluated in the patent are mannitol, sodium bicarbonate, lactose, polyvinyl pyrrolidone (PVP), arginine, and tartaric acid. The lyophilizates illustrated in the patent prepared with sodium bicarbonate exhibited dissolution times upon reconstitution of about two minutes or greater.

A study of "The Stability of Cyclophosphamide in Lyophilized Cakes" by Kovalcik and Guillory, J. Parenteral Science & Technology, 42, No. 1, 29-37 (1988) discloses sodium bicarbonate lyophilizates prepared using a 1:4 weight ratio of cyclophosphamide to sodium bicarbonate with a 5% water content of total weight of the lyophilizate. The sample cakes showed a 5% loss in potency when left at room temperature for 53 days and 4% loss in potency when stored at room temperature for 117 days.

Practical problems have occurred preparing a composition having a 1:4 ratio of cyclophosphamide to sodium bicarbonate in that special large vial sizes are required to obtain a lyophilizate cake. In addition, the solids of such ratios are not readily soluble and hydration time is undesirably long due to high sodium bicarbonate concentration and the amount of water necessary is greater than the sum of the mole equivalent of cyclophosphamide and the mole equivalent sodium bicarbonate.

It has also been unknown that pH levels should be kept at 8 or above in the lyophilization process in order to achieve a highly stable cake. When the pH of the bulk solution drops below 8, carbon dioxide is undesirably released and causes a reduction in effective concentration of sodium carbonate in the solution for lyophilization and adversely affects stability of the cake.

SUMMARY OF THE INVENTION

It has now been found that lyophilizates of cyclophosphamide having improved dissolution times and good shelf stability can be obtained using sodium bicarbonate as the excipient. In accordance with the present invention, the amount of water in the lyophilizate is preferably about equimolar to the amount of cyclophosphamide and the amount of sodium bicarbonate present in the lyophilizate. Lyophilizates in accordance with the present invention, generally contain about 50 to 300 parts by weight water and about 150 to 500 parts by weight sodium bicarbonate and about 100 to 500 parts by weight cyclophosphamide. In addition to dissolving quickly, these lyophilizates experience less than 5% loss in potency when stored at 37° C. for a period of six weeks.

Accordingly, one object of the present invention is to provide a lyophilizate of cyclophosphamide using sodium bicarbonate as an excipient which dissolves rapidly when reconstituted with water and which provides good shelf stability.

Another object of the present invention is to provide a lyophilizate wherein the lyophilizate contains water in an amount which is approximately equimolar to the amount of cyclophosphamide and sodium bicarbonate to about 60% in excess thereof.

Another object of the present invention is to provide a process for preparing a lyophilizate of cyclophosphamide having short dissolution time and good shelf stability.

These and other objects are achieved in accordance with the present invention which is described below in more detail.

DETAILED DESCRIPTION OF THE INVENTION

Previously, as disclosed in U.S. Pat. No. 4,537,883, unsatisfactory lyophilizates have been obtained from cyclophosphamide and sodium bicarbonate. In particular, the previous lyophilizates require 2 minutes or longer to dissolve for reconstitution. Contrary to the teachings in the patent, it has now been found that lyophilizates of cyclophosphamide and sodium bicarbonate having good shelf life and a dissolution time upon reconstitution with a suitable diluent on the order of 30 seconds can be obtained.

Conventional lyophilization techniques can be used in the present invention including the methods described in U.S. Pat. No. 4,537,883 among other methods known to those skilled in the art. Following lyophilization, in accordance with the present invention, the lyophilizate is hydrated. Hydration can be accomplished by aspirating water into the vial containing the lyophilizate using an ultrasonic spray nozzle which delivers a predetermined amount of water or by placing the vial in a humidity chamber having a relative humidity exceeding 85%. In addition, hydration techniques may also be accomplished by the processes disclosed in U.S. Pat. Nos. 4,659,699 and 4,537,883 which are incorporated herein by reference. A critical feature of the present invention is that the lyophilizate is hydrated such that it contains the aforementioned at least equimolar amount of water. While the compositions may be hydrated such that they contain water in excess of an equimolar amount, if the amount of water present in the lyophilizate exceeds an equimolar amount by more than 60% by weight based on the weight of cyclophosphamide, the stability of lyophilizate diminishes. If the lyophilizate contains less than an equimolar amount of water, a portion of the cyclophosphamide is present in the amorphous anhydrous form and the dosage is less stable. This is illustrated in the example below. By Karl Fisher analysis, the amount of water is preferably 15 to 20% by weight of the lyophilizate and more broadly 13 to 26% by weight of the lyophilizate.

The bulk solution is prepared as follows: a quantity of cyclophosphamide is added with mixing water for injection, sufficient to give a solution of cyclophosphamide which is about 30.4 mg/ml. The pH of the solution is adjustd with base, preferably sodium hydroxide, to about 8.2. Thereafter, sodium bicarbonate is added to the solution with mixing sufficient to give a solution containing 24.1 mg/ml of sodium bicarbonate.

The concentration of the sodium bicarbonate in the bulk solution may have an effect on the stability of the cyclophosphamide lyophilizate prepared from such bulk solution. This effect apparently is related to the pH of the solution. Lyophilizates prepared from solutions containing at least 1% sodium bicarbonate and still more preferably at least 2% provide superior shelf stability. This is also demonstrated in the example below. Higher concentrations of bicarbonate can be used in accordance with the invention, but with little effect on stability. Neutralization is not necessary if the reconstituted solution is administered in large volumes of saline in which case the effect of the reconstituted solution on the pH of the solution administered to the patient is negligible. Nevertheless, there is no indication that there is any advantage to using greater than 5% sodium bicarbonate in the bulk solution and for this reason concentrations of about 2 to 5% are generally used.

The lyophilizates of the present invention are preferably prepared by lyophilizing solutions containing about 1 to 5% (W/V) sodium bicarbonate and 1 to 4% (W/V) cyclophosphamide. Conventional lyophilization conditions can be employed to lyophilize the compositions. The conditions employed in the Example which follows are one example of those which can be used.

After lyophilization, the composition is hydrated. Hydration can be accomplished by aspirating water into the vial using an ultrasonic spray nozzle which delivers a predetermined amount of water or keeping the vial in a humidity chamber at 70-85% RH or humidifying the lyophilization chamber to 70-100% RH.

Taking into consideration the foregoing teachings, lyophilizates prepared in accordance with the present invention may contain about 100 to 500 parts cyclophosphamide, about 150 to 500 parts sodium bicarbonate; and about 50 to 300 parts water.

In one embodiment of the invention, these compositions contain cyclophosphamide and sodium bicarbonate in a weight ratio of about 1:0.5 to 1:1.5 and contain about 13 to 26% water.

In a preferred embodiment, these compositions contain cyclophosphamide and sodium bicarbonate in a weight ratio of about 1:0.5 to 1:1 and contain about 13 to 21% water.

In a still more preferred embodiment, the ratio of cyclophosphamide to sodium bicarbonate is about 1:0.75 to 1:0.85 and the amount of water is about 14 to 18%.

In a more specific embodiment of the invention, the weight ratio of cyclophosphamide to sodium bicarbonate is 1:0.8.

The effect of the sodium bicarbonate concentration of the pre-lyophilized solution and the water content of the lyophilizate on the stability of cyclophosphamide lyophilizates is illustrated in the following non-limiting example.

EXAMPLE 1

Lyophilizates of cyclophosphamide and sodium bicarbonate were prepared as follows:

Solutions (5 ml) containing cyclophosphamide (CP) and sodium bicarbonate ($NaHCO_3$) in the weight ratio indicated in the following table were placed in 10 cc vials. The samples were prepared using 20 mg/ml cyclophosphamide. Samples 1-8 and 10 were prepared using 30 mg/ml of sodium bicarbonate and sample 9 using 10 mg/ml of sodium bicarbonate. The vials were frozen in a lyophilization chamber for about 12 hours at a shelf temperature of −26° C. The chamber was then evacuated to a pressure of about 100 millitorr. The samples were maintained in the chamber at a shelf temperature of 0° C. for 16 hours and 25° C. for 8 hours. After lyophilization was completed, one sample (No. 1) was removed without re-hydration. This sample contained 12.9 weight percent of water based on the total amount of weight in the vial and which corresponds to the amount of water bound to the sodium bicarbonate in the lyophilizate. The balance of the samples were hydrated by placing them in an 85% humidity chamber and monitoring the weight gain. The amount of water in the lyophilizate expressed as a percent of the total composition and as a weight percent ratio of cyclophosphamide is shown in the table.

The samples were next subjected to an aging study wherein they were first assayed by HPLC, then placed in an oven at 37° C. for the periods indicated and finally reassayed. The loss in potency expressed as a percentage loss based on the initial assay is shown in Table 1.

TABLE 1

| Sample No. | CP:NaHCO$_3$ Wt. Ratio | pH | % Water* | % Water-CP** | Age (wks) | Loss in Potency (%) |
|---|---|---|---|---|---|---|
| 1 | 1:1.5 | 8.2 | 12.9 | 33.5 | 6 | 85 |
| 2 | 1:1.5 | 8.2 | 16.9 | 43.9 | 6 | 2 |
| 3 | 1:1.5 | 8.2 | 19.6 | 51.0 | 6 | 0-1 |
| 4 | 1:1.5 | 7.2 | 18.8 | 48.8 | 6 | 4 |
| 5 | 1:1.5 | 7.2 | 26.4 | 68.4 | 6 | 4 |
| 6 | 1:1.5 | 7.2 | 47.0 | 122.0 | 6 | 12 |
| 7 | 1:1.5 | 7.2 | 61.0 | 158.0 | 6 | 31 |
| 8 | 1:1.5 | 8.0 | 15.8 | 41.0 | 3 | 0 |
| 9 | 1:0.5 | — | 13.9 | 21.3 | 3 | 30 |
| 10 | 1:1.5 | 8.0 | 2.5−3.5 | 6.5−9.1 | 12 | 88 |

*percentage of total vial
**percentage based on cyclophosphamide

The results of the study show that Sample Nos. 2, 3 and 8 provided the highest stability, and Sample Nos. 4 and 5 provided moderately high stability. These samples are characterized in that the lyophilizates contain more than an equimolar amount of water. The samples prepared from solutions containing a high percentage of water in relation to sodium bicarbonate were far less stable (Sample Nos. 6, 7 and 9). Stability is very poor for Sample No. 1 which was not hydrated and Sample No. 10 which contained substantially less than an equimolar amount of water. It is concluded from this study that samples which were prepared at a pH greater than or equal to 8 and having a water content from about 15% to 20% based upon the total weight of the composition showed the most stability.

COMPARATIVE EXAMPLE 1

Comparative samples were made using Kovalcik and Guillory's hydration method to show the stability of cyclophosphamide/sodium bicarbonate lyophilizates at a pH of 8.2. Results are shown in Table 2.

TABLE 2

Stability Data of Cyclophosphamide Lyophilizate as Hydrated by Kovalcik and Guillory's Method

| Sample # | CP:NHCO$_3$ Wt. Ratio | % H$_2$O by KF | % Loss in Potency at 37° C./2 Months |
|---|---|---|---|
| 11 | 1:1.5 | 14 | 100 |
| 12 | 1:3.0 | 21 | 100 |
| 13 | 1:1.0 | 12 | 56 |
| 14 | 1:0.8 | 14 | 38 |
| 15 | 1:2.5 | 17 | 100 |

EXAMPLE 2

Samples were made as in Example 1 except that pH remained at 8.2 for lyophilization of all samples. Results are shown in Table 3.

TABLE 3

Stability Data of Cyclophosphamide Lyophilizate as Hydrated at 85% RH, 37° C. Storage

| Sample # | CP:NaHCO$_3$ Wt. Ratio | % H$_2$O by KF | % Loss in Potency at 37° C. 2 Months | 6 Months | 12 Months |
|---|---|---|---|---|---|
| 16 | 1:1.5 | 21 | 3 | 0 | 6 |
| 17 | 1:3.0 | 26 | 0 | 7 | 24 |
| 18 | 1:1.0 | 21 | 8 | 6 | 8 |
|  |  | 26 | 0 | 8 | 18 |
| 19 | 1:0.8 | 21 | 1 | 1 | 3 |
|  |  | 26 | 0 | 5 | 13 |
| 20 | 1:2.5 | 21 | 7 | 9 | 16 |
|  |  | 26 | 12 | 14 | 25 |

KF - Karl Fischer method for determination of the water content in the lyophilizate.

As can be seen from Tables 2 and 3, samples 14 and 19, having a cyclophosphamide/sodium bicarbonate weight ratio of 1:0.8, appear to be more stable compositions. In comparing the data from Table 2 and 3, the process used to form the samples in Table 3 appear to yield more stable compositions than does the hydration technique by Kovalcik and Guillory. Their superior stability may be due to the degree of hydration of the lyophilizate.

Separate samples were then run wherein the CP:NaHCO$_3$ weight ratio was kept constant at 1:0.8 and hydrated at 95-100% relative humidity inside the lyophilization chamber and the results are shown in Table 4.

TABLE 4

Solid State Stability of Cyclophosphamide/Sodium Bicarbonate (1:0.8) Stored at 37° C.

| Sample # | CP:NaHCO$_3$ Wt. Ratio | % H$_2$O by KF | % Loss in Potency at 1 Month | 2 Months | 6 Months |
|---|---|---|---|---|---|
| 21 | 1:0.8 | 13.9 + 0.3 (3 determinations) | 0 | 0 | 8 |
| 22 | 1:0.8 | 15.0% | 4 | 4 | 4 |
| 23 | 1:0.8 | 14.6 + 0.6 (4 determinations) | 5 | — | 2 |

As seen in Table 4, the cyclophosphamide lyophilizates of the invention all show excellent stability.

Having described the invention in detail and by reference to preferred embodiments thereof, it will be apparent that modifications and variations are possible without departing from the scope of the invention defined in the appended claims.

What is claimed is:

1. A lyophilized cyclophosphamide composition comprising cyclophosphamide, sodium bicarbonate, and water wherein the amount of water is about 13 to 26% by weight based upon the total weight of said composition and the weight ratio of cyclophosphamide to sodium bicarbonate is from about 1:0.5 to 1:1.

2. The composition of claim 1 wherein the weight ratio of said cyclophosphamide to said sodium bicarbonate ranges from about 1:0.75 to 1:0.85.

3. The composition of claim 2 wherein said water is present in an amount of about 13 to 21%.

4. The composition of claim 3 wherein said water is present in an amount of about 14 to 18%.

5. The composition of claim 1 wherein said composition is prepared from a solution of cyclophosphamide and sodium bicarbonate in water having a pH in the range of approximately 8 to 8.5.

6. The composition of claim 5 wherein said solution has a pH of approximately 8.2.

7. The composition of claim 5 wherein said composition is prepared by lyophilizing said solution and hydrating the lyophile at a relative humidity of 85% or greater.

8. A lyophilized cyclophosphamide composition comprising cyclophosphamide, sodium bicarbonate, and water, said cyclophosphamide and said sodium bicarbonate being present in a weight ratio of 1:0.8 and said water being present in an amount of about 14 to 18% based upon the total weight of said composition.

9. The composition of claim 8 wherein said composition is prepared from a solution of cyclophosphamide and sodium bicarbonate in water having a pH in the range of approximately 8 to 8.5.

10. The composition of claim 9 wherein said solution as a pH of approximately 8.2.

11. The composition of claim 10 wherein said composition is prepared by lyophilizing said solution and hydrating said lyophile at a relative humidity of at least 85%.

12. A hydrated lyophilized cyclophosphamide composition comprising cyclophosphamide, sodium bicarbonate, and water wherein the amount of water is about 13-26% by weight based on the total weight of the composition and the weight ratio of cyclophosphamide to sodium bicarbonate is from about 1:0.5 to about 1:1.5, and wherein said lyophilized composition is prepared from a bulk solution of cyclophosphamide and sodium bicarbonate in water having a pH in the range of approximately 8 to 8.5.

13. The composition of claim 12 wherein said bulk solution has a pH of about 8.2.

* * * * *